United States Patent
Mur et al.

(10) Patent No.: US 8,343,855 B2
(45) Date of Patent: Jan. 1, 2013

(54) NANOSTRUCTURED DEVICE

(75) Inventors: Pierre Mur, Crolles (FR); Cécile Oillic, Pont-Chateau (FR)

(73) Assignee: Commissariat A L'Energie Atomique, Paris (FR)

( * ) Notice: Subject to any disclaimer, the term of this patent is extended or adjusted under 35 U.S.C. 154(b) by 1025 days.

(21) Appl. No.: 12/094,211

(22) PCT Filed: Nov. 24, 2006

(86) PCT No.: PCT/EP2006/011300
§ 371 (c)(1),
(2), (4) Date: Oct. 27, 2008

(87) PCT Pub. No.: WO2007/059996
PCT Pub. Date: May 31, 2007

(65) Prior Publication Data
US 2009/0221447 A1 Sep. 3, 2009

(30) Foreign Application Priority Data
Nov. 25, 2005 (FR) .................... 05 11986

(51) Int. Cl.
*H01L 21/20* (2006.01)
*H01L 21/36* (2006.01)
*C12M 1/00* (2006.01)
*G11C 8/00* (2006.01)
*C40B 50/18* (2006.01)

(52) U.S. Cl. ............. 438/479; 435/283.1; 438/763; 365/230.03; 506/32

(58) Field of Classification Search ............... 435/283.1; 438/479, 763; 365/230.03; 506/32; 977/720
See application file for complete search history.

(56) References Cited

U.S. PATENT DOCUMENTS

| 6,159,620 A | 12/2000 | Heath et al. |
| 6,724,017 B2 * | 4/2004 | Semeria et al. ............ 257/183 |
| 2003/0111670 A1 | 6/2003 | Misra et al. |
| 2004/0114445 A1 | 6/2004 | Occhipinti et al. |

FOREIGN PATENT DOCUMENTS

| EP | 1 376 606 A1 | 1/2004 |
| WO | WO 03/052835 A1 | 6/2003 |
| WO | WO 2004/099068 A2 | 11/2004 |
| WO | WO 2005/105308 A1 | 11/2005 |

OTHER PUBLICATIONS

A. Shavel et al., Covalent Linking of CdTe Nanocrystals to Amino-Functionalized Surfaces, 6 CHEMPHYSCHEM 449-451 (2005).*
T. Baron et al., "Growth By Low Pressure Chemical Vapor Deposition of Silicon Quantum Dots on Insulator For Nanoelectronics Devices", Mat. Res. Soc. Symp. Proc., vol. 571 (2000) pp. 37-42.

(Continued)

*Primary Examiner* — Randy Boyer
(74) *Attorney, Agent, or Firm* — Millen, White, Zelano & Branigan, PC

(57) ABSTRACT

The invention concerns a nanostructured device (100) comprising a substrate (101), an intermediate layer (102), a zone (103) consisting of multiple three-dimensional structured sites (104) made of semiconductor material, having chemical species (106) fixed to the surface of said three-dimensional nanostructured sites (104). The inventive device is useful for making a biochip and an electronic memory. The invention also concerns a method for forming an electronic memory.

39 Claims, 8 Drawing Sheets

OTHER PUBLICATIONS

L. Hilliard et al., "Immobilization of Oligonucleotides onto Silica Nanoparticles for DNA Hybridization Studies", Analytica Chimica Acta, vol. 470 (2002) pp. 51-56.

M. Bawendi, "Nanocrystalites : Building Blocks for Quantum Dot Heterostructures", Solid State Communications, vol. 107, No. 11 (1998) p. 709.

* cited by examiner

NANOSTRUCTURED DEVICE

One subject of the present invention is a nanostructured device with a multitude of three-dimensional nanostructured sites for grafting chemical species. The device according to the invention can be used for manufacturing a biochip and an electronic memory. Another subject of the present invention is a process for forming an electronic memory.

Conferring very distinctive surface properties on the surface of a microsystem (microstructure) is a significant problem in the field of microtechnology and nanotechnology. It is even more important to be able to have these various properties on one and the same support.

Surface functionalization is often carried out by the reaction of an organic silane on an oxide layer, for example $SiO_2$. Numerous examples will be noted. The application of the organic layer may be carried out, for example, by immersing in a liquid phase (cf. "Nanoliter liquid metering in microchannels using hydrophobic patterns" *Anal. Chem.* 2002, 72, 4100-4109), in a gas phase, by embossing (cf. "Chemical nano-patterning using hot embossing lithography", Microelectronics Engineering 2002, 61-62, 423-428), by depositing, by spin-coating (cf. "Automatic transportation of a droplet on a wettability gradient surface", 7th International Conference on miniaturized Chemical and Biochemical analysis systems, Oct. 5-9, 2003, Sqaw Valley, Calif. (USA)), etc.

The immobilization of organic molecules on the supports requires the creation of an interface between the inorganic substrate (glass, silicon oxide, etc.) and the molecules of interest owing to the functionalization of the surfaces. Various substrate/molecules of interest pairs that have suitable chemical functional groups may be used in order to introduce a bond involving various interactions.

Currently, in the field of biology, two main techniques for immobilizing biological molecules are commonly used for preparing nucleic acid biochips. Depending on the type of application desired, the probes are immobilized covalently or non-covalently by one of the ends on a solid support. The implementation of the biochips is carried out either by "on-chip" technologies where the oligonucleotide probes are synthesized in situ on the support or by "off-chip" technologies where the probes are first synthesized, purified and controlled before being grafted onto the substrate thanks to a deposition robot.

Currently, most of the biochips sold are produced on a glass support, functionalized by various functional groups. Although the quality and the reliability of most biochips no longer need to be proven, the functionalization chemistry used on the planar surfaces generates a single functional group per molecule whether this is from the support or from the nucleic acid. However, the increase of active sites onto which the probes may be bonded makes it possible to increase the capacitance of probes immobilized on the support, hence a better sensitivity of the response in terms of hybridization.

Various strategies have been envisaged for improving the sensitivity of the detection of biological events. A first route proposed is to increase the hybridization reaction density at the surface of the biochip. This may be carried out by increasing either the specific surface area available by using porous supports or the density of grafted probes by using three-dimensional surfaces (Yap et al., Langmuir 2005, vol. 21, No. 12).

Several teams have worked on the production of a pseudo three-dimensional structure based on a tie system known as "dendrimers". Successive studies have made it possible to limit the number of steps for producing this support; nevertheless, the manufacture of the support necessitates, all the same, producing the support and the components to be transferred independently, which involves a high cost and a large number of steps (Le Berre, Nucl. Acids Res. 2003, 31/No 16 e 88).

Other authors have used nanoparticles that are modified and immobilized on planar surfaces as another route for reducing the steric hindrance at the surface and increasing the probe density for hybridization. Nanoparticles, such as supports for receiving these components, may be of very diverse natures (metallic, polystyrene latex, silica on glass, silicon, polystyrene/polybutadiene, etc.). However, this method, like the process described previously, requires the transfer of the components to a surface prepared separately, hence a production of the biochip in several steps and a high cost.

In the case of charge storage memories, one of the solutions used for increasing the capacitance of Flash memory arrays, without having to decrease the individual cell size, is to use multi-level programming. Reference is then made to multi-level memories (or MLC for multi-level cell). Multilevel programming makes it possible to code several bits in the same cell. It consists in quantifying the charge stored on the floating gate in $2^n$ (n>1) states in order to have the possibility of coding "n" bits rather than one alone. For this, a sequence of bits is assigned to a specific voltage range. For example, each cell may therefore take the states 00, 01, 10 or 11, corresponding to an equal number of threshold voltage levels, which themselves depend on the charge stored in the floating gate of the transistor. This concept was presented in 1995 by Intel who then used it in a family of products known as "Strataflash". The implementation of multi-level programming is not however easy. The difficulty is in controlling, with precision, the charge stored on each of the states of the cell and of discriminating them with precision (precise reading of the various threshold voltage levels).

The capacitances of flash memories have not stopped increasing with the continuous reduction of the individual cells linked to the miniaturization of the devices. This race to the integration density and also to the reduction of operating times has made it possible to increase the density of memories from 64 Mb in 1997 to 512 Mb currently for NOR flash and 2 Gb for NAND flash. Production of 8 Gb NAND flash prototypes with 63 nm technology using the MLC (multi-level cell) technique were also presented by Samsung at the end of 2004.

However, several technological obstacles begin to oppose the pursuit of this miniaturization. The reduction of the dimensions of the memories is accompanied by the reduction of the thicknesses of the dielectrics, in particular of the gate oxide. The tunnel oxide thickness will be 8-9 nm for NORs and 6-7 nm for NANDs in 2007. The reduction in the thickness of this oxide to below 8 nm gives rise to an increase of leakage currents through the latter, by a direct tunnel effect or by defects in this oxide, the retention thereof is then effected. The decrease in operating voltages in order to reduce the energy consumption in order to achieve low usage voltages (~1 to 2 V) for CMOS (complementary MOS) logic transistors is another difficulty to be solved.

In order to overcome these difficulties, novel architectures and novel materials are currently being studied for flash memories.

The replacement of the polycrystalline silicon floating gate by discrete trapping sites has been proposed. One of the advantages of this type of traps is the electrical insulation between trapping sites.

The presence of a defect in the tunnel oxide will only affect the charge located on top of the defect. In this type of memory, it is also possible to code two bits (or four states), due to the localized nature of the stored charge. Two main types of memory having discrete storage sites may be cited; nitride memory, of SONOS (silicon oxide nitride oxide silicon) type and silicon nanocrystal memory.

Nanocrystal memories have an increased robustness to the defects in the tunnel oxide and therefore make it possible to reduce the thickness (down to 5 nm) of the latter and thus to reduce the write and erase voltages and the programming times. However, nanocrystal memories also have their limitations which are, in particular, the low capacitive coupling between the control gate and the floating gate. This makes it necessary to keep the programming voltages at a high level, and partly reduces the benefits linked to the reduction of the tunnel oxide. Furthermore, the threshold voltage shifts obtained are relatively low, due to the low level of covering of the active surface by the silicon nanocrystals (between $5 \times 10^{11}$ and $10^{12}$ cm$^{-2}$). Finally, the dispersion in the size of the nanocrystals and in the density leads to a dispersion of the memory characteristics. Other types of non-volatile memories which are not based on semiconductor materials are also the subject of advanced studies. Among the most promising routes, mention may be made of ferromagnetic memory (Fe-RAM), magnetic memory (MRAM) and phase change memory (PCRAM). These various approaches also have their advantages (rapidity of the write/read times, excellent durability, etc.) and their disadvantages (reduction of the dimensions, maturity, cost, etc.).

Novel approaches, that call upon chemistry, are beginning to be the subject of advanced research. These are molecular memories. They have the potential to go beyond the limits of semiconductor memories. This is because synthetic molecules offer numerous advantages compared to conventional semiconductors: three-dimensional assembly, synthetic materials that make it possible to obtain properties to suit, miniaturization approaching that of biological structures, possibilities of interface with living systems and above all low manufacturing costs. The hybridization of these molecules with current CMOS systems will probably be the first phase of industrial development.

In these devices, the charge is stored at one or more metallic atoms, the latter being complexed by organic molecules. In order to be able to store a charge, these metallic atoms must have redox properties. The molecule then has at least two charge states, one of these states being the "erased" state and the other the "written" state. Passing from one state to another is carried out by charge transfer via an oxidation-reduction reaction mechanism, by applying a certain polarization voltage to the molecule.

The use of organic compounds having redox properties such as metallocenes and metalloporphyrins has been proposed as a charge storage system in a field-effect transistor. The complexed organic molecules are covalently attached either directly to the transistor channel or to the tunnel oxide surmounting this channel. Tying organic molecules to an inorganic substrate, such as silicon, requires a functionalization of these molecules and/or a surface treatment of the substrate in order to be able to form the covalent bond.

These charge storage molecular memories have advantages, such as the reduction of the dimensions and the use of low supply voltages. This is because the standard redox potentials of these molecules vary, on average, from +2 V to −2 V. Moreover, the use of molecules having more than two redox states would allow the development of a multi-bit memory.

The problem to be solved was to overcome the aforementioned drawbacks and to create a device having improved properties, that is to say especially a device with an excellent stability and a good detection sensitivity compared to the devices of the prior art. Another aspect of the problem to be solved was to offer the possibility of manufacturing the devices according to the invention at lower cost, in a limited number of steps and in a controlled and reproducible manner.

This problem is therefore solved by a nanostructured device comprising a substrate, an intermediate layer, a zone consisting of a multitude of three-dimensional nanostructured sites that mainly consist of a semiconductor material, having chemical species tied to the surface of said three-dimensional nanostructured sites.

The device according to the invention makes it possible to increase the specific surface area of the solid support, obtained by the manufacture of nanoscale-sized silicon islands, with a high density and a more or less uniform spatial distribution. The modification of the geometry of the substrate, that is to say passing from a two-dimensional to three-dimensional geometry, makes it possible to significantly increase the specific surface area of the support. The use of a solid support comprising nanostructures therefore makes it possible to increase the available surface area compared to a planar surface, without however increasing the dimensions of the support. The nanostructured sites are arranged in a regular or irregular manner in geometrical shapes which may be chosen according to the desired application. Non-limiting examples of the geometrical shapes of the arrangement of the sites are circles, squares, overlapping lines, etc., which are mainly known in the art.

Preferably, the surfaces of the three-dimensional nanostructured sites are equipped with a tie layer which, in one particular embodiment, is porous. The tie layer is produced by a chemical modification. The chemical modification may also be, for example, the 2-step conversion of an epoxide functional group to an aldehyde functional group in order to graft thereto molecules equipped with amine-type groups. Similarly, an ester functional group may be converted to an acid functional group in order to result in hydrophilic surfaces that are also reactive toward $NH_2$ functional groups. The device of the present invention additionally comprises a successive functionalization.

It is advantageous that the surface of the tie layer be equipped with chemical coupling functional groups to allow grafting of organic molecules.

Preferably, the substrate is made from a material comprising silicon, germanium, quartz and mixtures of said materials.

In one preferred embodiment, the intermediate layer is a dielectric or insulating material. The dielectric material is chosen from oxides, nitrides, oxynitrides, carbides, oxycarbides and silicates of Si, Al, Hf, Zr or Ti.

It is preferred that the three-dimensional nanostructured sites be separated from one another and be grains having a hemispherical or spherical shape. In advantageous methods of operation, the grains have a diameter between 2 and 150 nm and the density of the grains on the intermediate layer is in the range between $10^6$ and $10^{12}$ cm$^{-2}$, preferably between $10^9$ and $10^{12}$ cm$^{-2}$. It is also possible that the grains be porous. In order to increase the sensitivity of a device according to the invention, the ratio of these two parameters should be optimized: it has been observed that too high a grain density will result in the coalescence of the grains, losing the advantage of the increase of specific surface areas. Therefore, densities of $5 \times 10^{11}$ to $2 \times 10^{12}$ cm$^{-2}$ and grain diameters (sizes) of 5 to 10 nm or densities of $10^8$ to $10^{10}$ cm$^{-2}$ and sizes of 80 to 100 nm are preferred.

Advantageously, the grains used within the context of the present invention are made of conductor or semiconductor materials. The conductor or semiconductor materials are chosen from those from the group comprising silicon, crystalline or amorphous carbon, optionally n- or p-doped, and metals, for example nickel, platinum or tungsten. The preferred metal is nickel. The preferred materials are silicon, germanium, doped carbon in crystalline or amorphous form (graphite, carbon nanotubes, single-crystal or polycrystalline diamond) or a semiconductor/metal alloy, for example metal silicide.

In the case where the grains are made of carbon and when the intermediate layer is made of oxide, this layer will be deposited.

Among the grains which may be used according to the invention, three types of grains (or nanostructured sites) are especially preferred, two of which are derived from the growth of rough polycrystalline silicon and the third based on the production of silicon nanocrystals. The silicon nanostructures are produced on a dielectric, in particular on a silicon oxide, by chemical vapor deposition processes mainly known in the art.

The chemical species are chosen from nucleic acids, peptides, proteins, enzymes, antibodies, lipids, their biological partners, compounds having redox properties such as metallocenes, metalloporphyrins and polyoxometallates.

The invention therefore also applies well to the field of biology, in particular for the immobilization of biological macromolecules such as nucleic acids, lipids, proteins (peptides, enzymes, antibodies, etc.) or their molecular partners, enabling the production of biochips based on a device according to the invention.

Biochips comprising a multitude of devices according to the invention are obtained by a process which is yet another aspect of the present invention.

This process comprises the following successive steps:
a) providing a substrate;
b) forming an intermediate layer on the surface of the substrate;
c) forming three-dimensional nanostructured sites on the intermediate layer; and
d) tying the chemical species to the surface of the three-dimensional nanostructured sites.

This process according to the invention offers an easy option for the manufacture of devices according to the invention. More particularly, it offers the option of manufacturing biochips with reactive sites that have an increased specific surface area.

In one particular embodiment, a tie layer is deposited over each nanostructured site in order to facilitate the step d) of tying the chemical species. This tie layer is preferably activated by a treatment with a compound having functional groups capable of attaching chemical species by a chemical bond, preferably by a covalent bond. In another embodiment of the present invention, this bond may also be an ionic or other bond.

For biochip applications, the chemical species to be tied in step d) are chosen from nucleic acids, peptides, proteins, enzymes, antibodies, lipids, their biological partners, compounds having redox properties such as metallocenes, metalloporphyrins and polyoxometallates.

The invention also applies to the field of microelectronics, especially for producing charge storage memories, the organic molecules grafted to the nanostructures of the invention then being capable of storing or favoring the storage of charges.

In one particular embodiment, the chemical species are covered with a dielectric layer. Furthermore, a layer made of a conductive material is located on top of the dielectric layer. This allows the production of electronic memories.

The problem of the invention is also solved by an electronic memory comprising a multitude of devices according to the invention which are interconnected.

The multitude of devices forms a control gate and the electronic memory according to the invention comprises a source and a drain as well as an encapsulation layer which is made of an electronically conductive material or of an electrically insulating material.

A third aspect of the problem to be solved was a process for manufacturing an electronic memory according to the invention, the process comprising the following successive steps:
a) providing a silicon substrate that has a multitude of sacrificial gate zones, a source, a drain, a silicided zone and an encapsulation layer;
b) removing the dummy gate (or sacrificial gate) delimited by the gate zone down to the surface of the substrate to form a well of defined size;
c) forming an insulating layer over the surface of the substrate obtained in step b);
d) depositing nanostructured sites over the insulating layer at the bottom of the well;
e) tying chemical species to the surface of the nanostructured sites;
f) applying a layer of a control dielectric to the tied chemical species; and
g) depositing a layer made of a conductive material onto the control dielectric layer.

Preferably, the process according to the invention is characterized in that the step b) will be carried out by successive etching of one part of the layers of the sacrificial gate.

The formation of the insulating layer will preferably be carried out by oxidation of the substrate. The deposition of nanostructured sites will be carried out by a method chosen from CVD, LPCVD and inoculation/annealing.

Moreover, a tie layer is deposited over each nanostructured site which is preferably a grain as mentioned above. The tie layer is activated by treatment with a compound that has functional groups capable of attaching chemical species via a chemical bond, preferably via a covalent bond. In other embodiments another bond, for example an ionic bond or any other type of bond may be envisaged.

In one preferred method of operation, the chemical species are molecules having at least two stable oxidation states such as polyoxometallates, metallocenes, metalloporphyrins, etc.

The layer of a control dielectric is formed by low-temperature deposition or by addition of an electrolyte gel.

BRIEF DESCRIPTION OF THE DRAWINGS

Other features and advantages of the invention will emerge from the description which follows, with reference to the figures of the appended drawings. The exemplary embodiments described with reference to the appended drawings are in no way limiting.

FIG. 1 illustrates the principle of a nanostructured support 100 with a substrate 101, a dielectric layer 102, nanostructured sites 103 and chemical species 104, in particular organic molecules tied to the nanostructured sites. The materials of the layers 101, 102, of the nanostructured sites 103 and the nature of the chemical species are described above.

Figure 1:
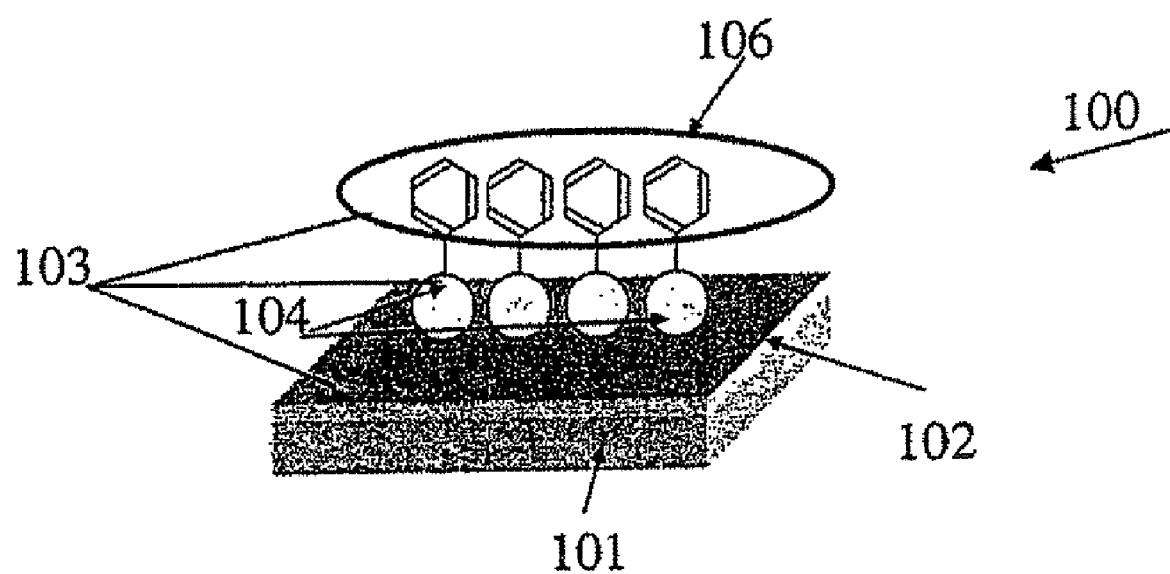
FIG. 1 illustrates the principle of a device according to the invention.

The device of the present invention could be used for preparing chemical and biological sensors, within the context of producing DNA chips, protein chips, sugar chips, peptide chips, small-organic-molecule chips for therapeutic purposes, and also for preparing microfluidic systems that require functionalization of their walls.

Moreover, the process of the present invention could be used for preparing any microelectronic device.

EXEMPLARY EMBODIMENTS

Example 1

Formation of Rough Polycrystalline Si by LPCVD Deposition

The deposition of the grains (nanostructured sites) as a rough layer of silicon may be carried out directly by low-pressure vapor deposition. Under optimal pressure and temperature conditions, the growth of the grains occurs directly on the silicon oxide via a permanent supply of silane. The silicon atoms are adsorbed at the surface and their successive migration makes it possible to increase the size of the grains.

A vertical LPCVD (low pressure chemical vapor deposition) reactor was used. Depositions were made over a crystalline silicon substrate covered with a thermal oxide having a thickness of around 1000 Å. For each deposit of 20 minutes, the temperature varied from 570 to 580° C. and the silane pressure from 0.19 to 0.21 torr.

The operating point that gives the largest surface growth is located at a temperature of 580° C. and a silane pressure of 200 mtorr. The initial surface was increased by 43.7%, the roughness rms was 16 nm and the maximum height variation between two points was 106 nm.

During the deposition, the silicon atoms are adsorbed either directly onto the seed which has a site favored for nucleation, or the atom adsorbed migrates over the $SiO_2$ surface. The surface migration takes place until a seed or an atom already attached to the seed is encountered. These two phenomena gradually increase the size of the core until a grain is formed. A system of grains of hemispherical shape attached to the $SiO_2$ layer is obtained. The layer is therefore not strictly continuous. The $SiO_2$ surface may be visible between two grains.

Another process has been used within the context of the invention to form the rough polysilicon film by thermal decomposition of the pure silane in a vertical LPCVD furnace then annealing. Before the deposition, the pressure in the chamber of the furnace is reduced to 1 mtorr. The layers are deposited on a thermally oxidized silicon substrate. The conditions to be brought together during the deposition in order to achieve the largest growth are the combination of pressure and temperature (0.2 torr, 567-570° C). The deposition is followed by an in situ 20 min annealing at a temperature of 570° C.

The change that makes it possible to pass from the surface morphology of a smooth polysilicon film to that of a rough polysilicon film takes place for a temperature variation during the deposition of a few degrees. This passing from one surface state to the other is abrupt. On the other hand, the change that makes it possible to pass from the rough morphology to that of a smooth film is fairly gradual.

For a set pressure (0.2 torr), the temperature increase led to a rapid increase in the number of grains. At low temperature (550-560° C.), an amorphous and smooth surface with a few scattered hemispherical grains is observed, then the number of grains increases until they adopt a more cylindrical shape, well separated from one another so that the film deposited becomes discontinuous (565-570° C.). For higher temperatures (>575° C.), a smooth, continuous and polycrystalline film is obtained.

The thickness of the layer deposited plays an important role in the surface morphology. At 570° C., as the thickness of the layer increases (from 60 nm to 300 nm), the density of the grains decreases and the size of the grains increases.

For a set temperature (570° C.), the increase in pressure leads to a rapid decrease in the density of the grains. The density is practically zero at 1 torr.

TEM observation makes it possible to detect the presence of crystalline particles in the amorphous silicon layer deposited at the transition temperature. This also makes it possible to see that the rough polysilicon is characterized by a grain growth of favored direction <311>. The growth of the rough polysilicon is independent of the substrate ($SiO_2$, $Si_3N_4$, Si). When the annealing time increases, the size of the grains (nanostructured sites) increases but the density remains constant.

Example 2

Growth on Amorphous Silicon

Another method that can also be applied within the context of the present invention makes it possible to control the density and the characteristics of the grains. This process takes place in three in situ steps. The first step is a deposition of doped amorphous silicon produced at 540° C. The second, known as "seeding" (nucleation) is carried out at a low silane pressure ($5 \times 10^{-5}$ torr), at 560° C. for 5 min. It makes it possible to generate nuclei at the surface of the amorphous layer. This seeding is followed by an isothermal (600° C.) annealing at low pressure ($3 \times 10^{-8}$ torr).

The presence of native oxide, of carbon-based impurities and the high concentration of dopants in the amorphous silicon layer prevents the surface migration and therefore the growth of the grains. The effects of the pressure of the system and of the partial pressure of the silane are not as important as those of the temperature.

The deposition temperatures must be as low as possible since crystallization phenomena of the layer prevent the formation of grains at certain places of the sheet. The nucleation density increases with the seeding time.

The annealing step is not involved in the density of the grains set during the seeding step, but on the other hand makes it possible to define their size.

The concentration of dopants is critical for the conversion of the HSG. This is because the phosphorus at the surface acts as a nucleation site and prevents the surface mobility of the atomic silicon during annealing. This is the reason why the doped layer must be covered by an intrinsic amorphous silicon layer.

These two routes allow rough polycrystalline silicon to be formed. The nanostructured sites obtained are surfaces said to have "large" grains (100-150 nm in diameter), produced in an industrial-type furnace.

Example 3

Silicon Nanocrystals

Nanocrystalline silicon islands are formed by CVD during the first moments of growth of a polysilicon film on $SiO_2$ by silane chemistry CVD. The deposition temperatures, close to 600° C., are identical to those used for depositions of polycrystalline silicon. The density and the size of the nc-Si may be controlled by the deposition conditions: pressure and temperature, but also by the chemical properties of the substrate.

Nanodots (nanostructured sites in the meaning of the invention) are produced by CVD (chemical vapor deposition) on a dielectric by controlling the first stages of the growth of silicon films. The growth is carried out starting from a silane, disilane or dichlorosilane precursor. The precursor is diluted in a carrier gas such as hydrogen or helium. The total pressure is 20 torr. The depositions are carried out between 400 and 700° C. with a partial pressure between a few millitorrs and a few hundred millitorrs.

The density of the nanodots may be adjusted between $10^9$ and a few $10^{12}$ cm$^2$ and the size between 2 and 20 nm.

To improve the size dispersion of the nc-Si, it is necessary to separate the nucleation and the growth of the nc-Si. In order to achieve this, a two-step CVD process is used.

In the first step, silicon nuclei (nanostructured sites) are formed at the surface of the substrate by silane chemistry CVD.

In the second step, dichlorosilane (DCS) is used as a precursor since it allows a selective growth of the silicon on the nuclei formed during the nucleation step, without formation of new nc-Si.

Example 4

Figure 3:
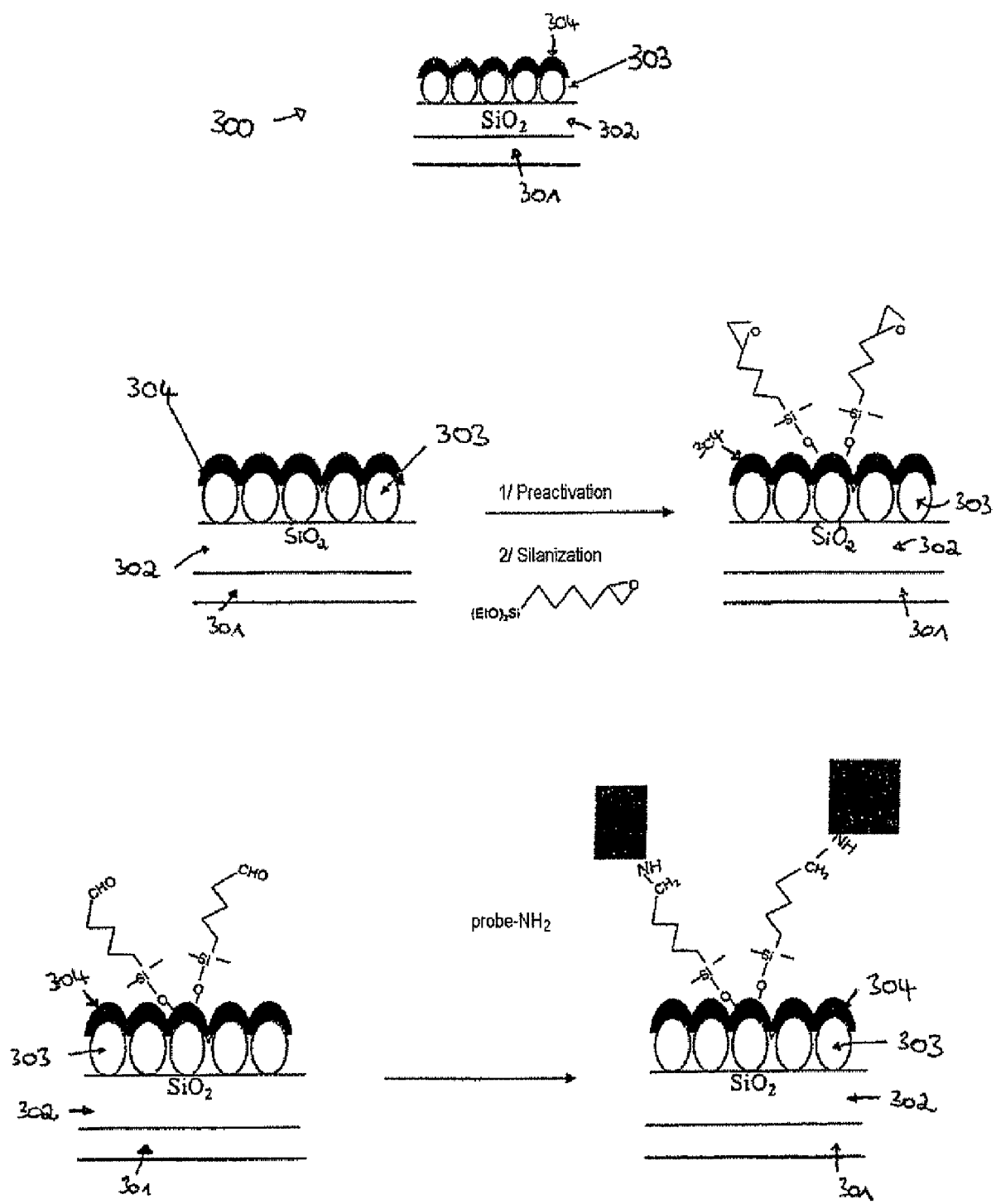
FIG. 3 illustrates the functionalization of the nanostructured sites in a process for preparing a device according to the invention followed by the immobilization of biological probes.

Preparation of a Biochip with a Device According to the Invention (FIG. 3)

By way of example, the step of forming the intermediate layer 304 over silicon grains 303 is carried out by thermal oxidation of the silicon, comprising Si—O—Si bonds capable of attaching a functionalization layer. The oxidation step may be carried out by using an $O_2/H_2O$ or $O_2/HCl$ mixture in a controlled atmosphere, that makes it possible to obtain amorphous silicon oxide layers of variable thickness. The device 300 obtained is represented in FIG. 3a. The device 300 also comprises a support 301 made of silicon and an intermediate layer 302 made of $SiO_2$. The Si grains 300 are applied to the layer 302 as described above.

The preactivation step is a step of cleaning and of rehydrating the surface of said support. It allows the creation of silanol groups Si—OH at the periphery of the nanostructures 303 starting from siloxane bridges Si—O—Si necessary for the attachment of the supplementary functionalization layer 304 by covalent bonding. This step is carried out in a basic/acid and/or oxidizing medium or by $O_2$ plasma.

The step of functionalizing the surface of said nanostructured support is carried out by silanization by means of a silanization reagent comprising functional groups capable of directly or indirectly attaching the molecules of interest, such as for example epoxide or aldehyde groups, via successive chemical conversions.

By way of example, the silanization step may be carried out using a silanization reagent having an epoxide functional group such as 5,6-epoxyhexyltriethoxysilane, 3-glycidoxypropyltrimethoxysilane or else an amine silanization reagent such as 3-aminopropyltriethoxysilane.

Depending on the organosilane used for the silanization step, it is sometimes necessary to carry out other chemical conversions so that the functionalized nanostructured supports thus obtained can then be stored and/or used directly for the immobilization and/or the synthesis in situ of molecules, in particular of biological molecules. Following the functionalization cited in the above example, various steps make it possible to convert the epoxide functional group to an aldehyde functional group, this chemical group being capable of allowing the covalent grafting of the biological probe modified by an —$NH_2$ functional group.

The thus functionalized nanostructures may be used as a miniaturized diagnostic tool, depending on the nature of the molecules of interest attached, as a DNA chip, for example for producing hybridization reactions with complementary targets, as peptide chips, polypeptide chips or protein chips, for example for detecting an antigen-antibody type response. The detection of biological recognition may be carried out by the use of marked, fluorescent, radioactive or chemically marked reagents or by any other type of detection method.

Figure 2A:
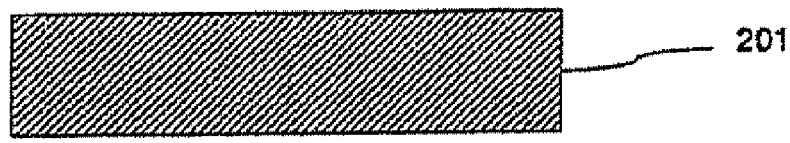
FIG. 2 illustrates a process for preparing a device according to the present invention.
Figure 2B:
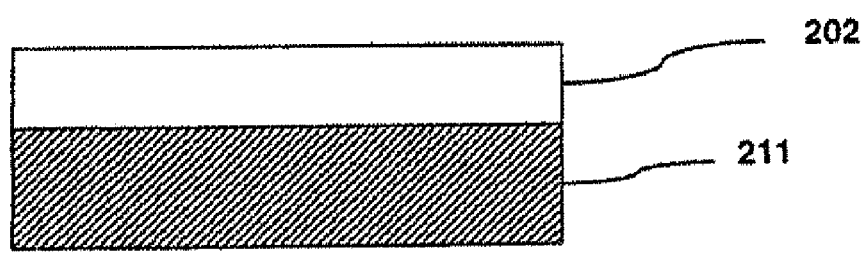
Figure 2C:
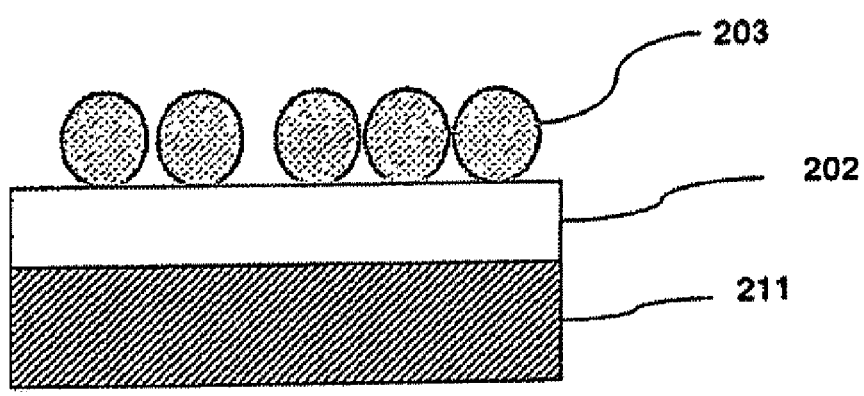

FIG. 2A illustrates a process for preparing a biochip:

A substrate 201, for example made of silicon (100), germanium or quartz, is covered (2B) with a dielectric 202 produced, for example, by oxidation of the latter or deposited directly onto the substrate 201 or deposited onto the substrate 201 by CVD or PVD methods. The substrate 201 may comprise zones said to be patterned or active in the meaning used by the present invention. The thickness of the dielectric layer 202 is typically around 100 nm.

In the case of a silicon substrate, the dielectric may be produced by thermal oxidation of the substrate 201 using the standard oxidation processes of microelectronics. Typical conditions are, for example, 800-1000° C. in a humid or dry environment. These oxidation processes may take place either in a humid environment with dilution of water in an inert carrier gas such as nitrogen, or in a dry atmosphere such as oxygen or oxygen+hydrogen chloride or DCE, or in the presence of water vapor or any other oxidizing atmospheres used in the field of microelectronics. When the dielectric 202 is deposited, the latter may be, for example, a silicon oxide or a silicon nitride or else a dielectric with a high dielectric constant such as, for example, an oxide or a silicate of a metallic material, such as, for example, $HfO_2$, $HfSiOx$, $Al_2O_3$, $ZrO_2$, etc. In order to produce these dielectrics, the processes and equipment from the microelectronics sector are used. The thickness of the dielectric may vary between 1.2 and a few 100 of nanometers depending on the requirements.

The nanostructured sites 203 (the "grains") are then produced. When the latter are made of silicon, they are manufactured by using technologies described in the prior art. The CVD or LPCVD deposition techniques of silicon are used. For this, a silicon precursor, for example silane, dichlorosilane, disilane, is used during a process having one or more steps, for example between 500° C. and 700° C. The density of the nanostructured sites is between $10^9$ and $10^{10}$ cm$^{-2}$.

Figure 2D:
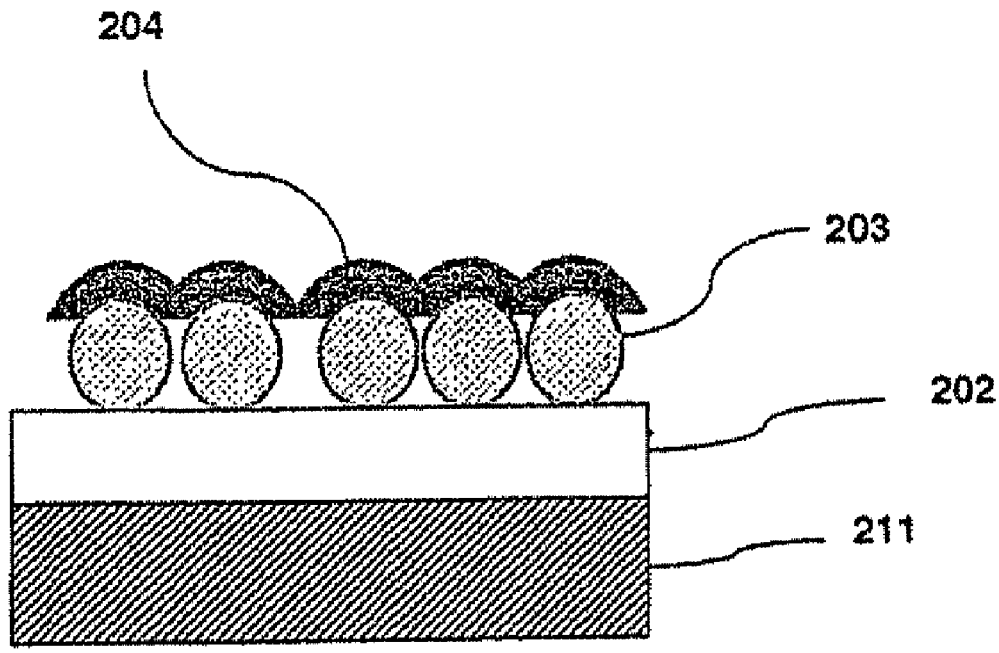

FIG. 2D describes the optional formation, depending on the targeted application, of an intermediate tie layer 204. This intermediate tie layer 204 is obtained at the surface of the nanostructured sites 203 by various chemical processes, for example by deposition, oxidation, chemical and/or electrochemical treatment. Preferably, it is produced by thermal oxidation of the nanostructured sites 203 between 600° C. and 1000° C. in a humid or dry oxidizing atmosphere. The thickness of this layer 204 is around 50 nm.

This intermediate layer, completely or partly made from one material, must be capable of providing, at the periphery, functional groups that are capable of allowing the attachment of another tie layer and/or the attachment or the synthesis in situ of molecules of interest, and capable of making it possible to limit the coupling of the visible radiation likely to be emitted by the biochip following an excitation by a read device with said support, in the particular case of producing optical detection biochips. The thickness of this tie layer is optimized depending on the targeted application.

Figure 2E:
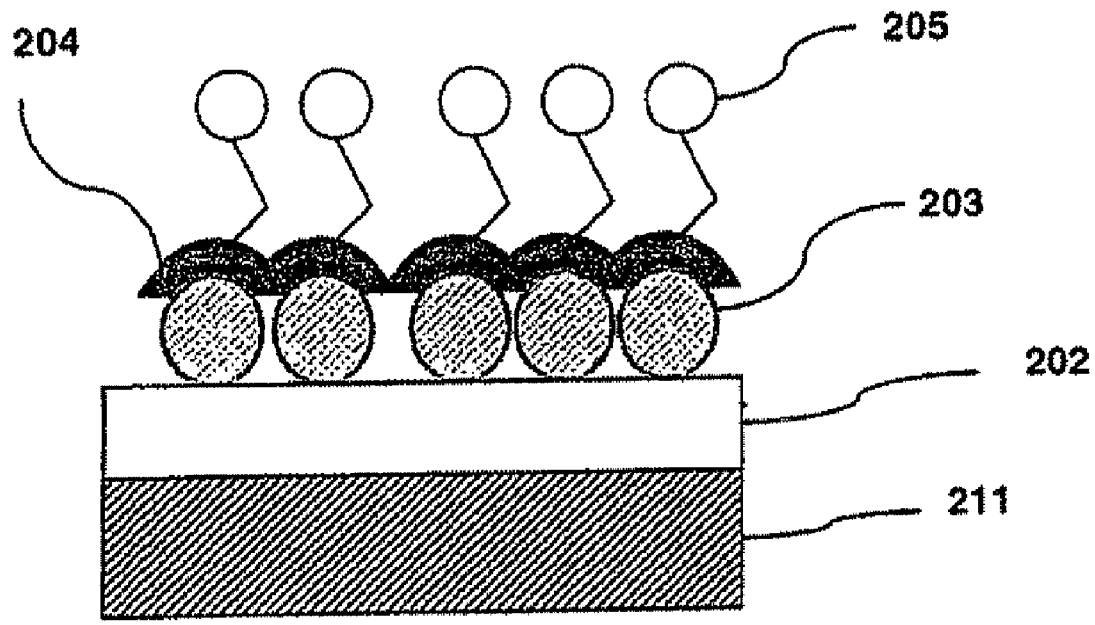

Before grafting the molecules of interest 205 (FIG. 2E) such as, for example, molecules of nucleic acid (oligonucleotides, PCR product, etc.), lipids, proteins (peptides, enzymes, antibodies, etc.) or their biological partners, there is an optional preactivation of the functional groups of the intermediate layer of the support in order to obtain an activated functionalized surface, and formation of a covalent bond between said functionalization layer and said intermediate and optionally activated layers, in order to obtain a solid support comprising functionalized nanostructures. The intermediate layer 204 is preactivated by an oxygen plasma (600 W, $O_2$=23 sccm). The preactivation enables the creation of silanol groups Si—OH at the periphery of the nanostructures starting from siloxane bridges Si—O—Si, necessary for the attachment of the supplementary functionalization layer by covalent bonding.

After preactivation, treatment of the intermediate layer 204 is carried out by silanization using a silanization reagent that has an epoxide functional group such as 5,6-epoxyhexyltriethoxysilane.

Next, an acid hydrolysis treatment and a liquid-phase oxidation make it possible to form aldehyde groups that make it possible to graft the probe oligonucleotide, modified by an amine ($NH_2$) functional group (5' $NH_2$: TTTTTGATAAACCCACTCTA).

The thus grafted probes are then hybridized by complementary targets (CATAGAGTGGGTTTATCCA) marked by the fluorophore Cy3 for which the excitation wavelength is 550 nm and which reemits at 570 nm.

The hybridization is then controlled by an optical analysis using a Genetaq IV scanner from the Genomic Solutions brand by Perkin Elmer. The detection is carried out at 543.5 nm.

Figure 5:
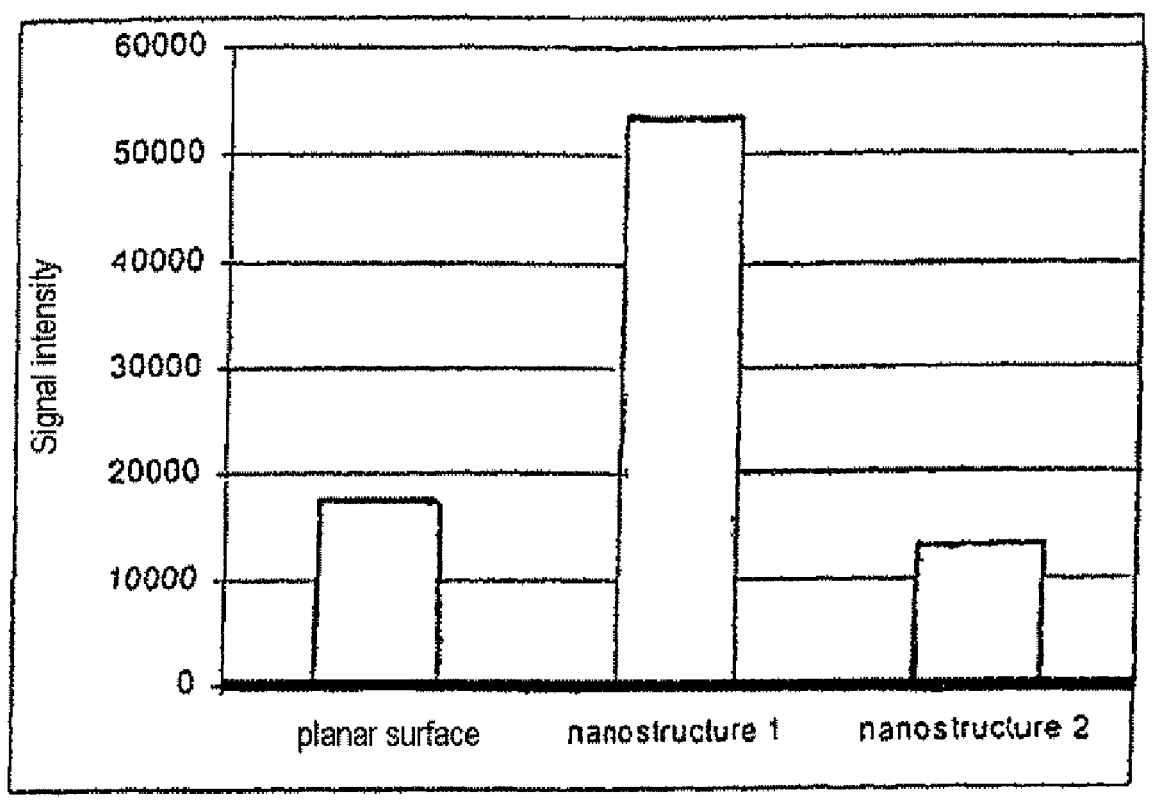
FIG. 5 illustrates the detection sensitivity of a device according to the invention compared to a device according to the prior art.

FIG. 5 illustrates the detection of the hybridization of the aforementioned probes with the abovementioned targets on devices according to the invention (nanostructure 1) compared a device prepared according to the prior art (planar surface). The density of the nanostructured sites on the substrate was $2\times10^9/cm^2$ with the grains deposited having a diameter of 33 nm.

The intensity of the signal using a planar substrate, that is to say the direct application of the probes onto a planar surface without the intermediary of nanostructured sites made of semiconductor materials, is much weaker than the signal obtained after the hybridization on the nanostructured sites of a device according to the invention. Specifically, it can be seen in FIG. 5 that a lower density (nanostructure 2 with larger grains) compared to nanostructure 1 does not make it possible to increase the specific surface area of the surface significantly and almost no difference is seen between a planar surface and the nanostructure 2, with even weakening of the signal intensity being seen.

In order to increase the grafting density, several variants may optionally be envisaged. The nanostructures 203 before the optional formation of the intermediate tie layer may be rendered porous by chemical and/or electrochemical treatment processes or any other porosification treatment.

Next, the optional formation, depending on the targeted application, of an intermediate tie layer 204 is obtained at the surface of the nanostructures 203 by various chemical processes, for example by deposition, oxidation, chemical and/or electrochemical treatment. This intermediate layer, completely or partly made from one material, must be capable of providing, at the periphery, functional groups that are capable of allowing the attachment of another tie layer and/or the attachment or the synthesis in situ of molecules of interest, and capable, in the case of a biochip, of making it possible to limit the coupling of the visible radiation likely to be emitted by the biochip following an excitation by a read device with said support, in the particular case of producing optical detection biochips. The thickness of this tie layer 204 is optimized depending on the targeted application. In the case where this tie layer is obtained by oxidation, the thickness of the oxide of the nanostructures is adjusted in order to retain the increase in the specific surface area generated by the nanostructures and to obtain a multilayer suitable for the targeted application. The oxide thickness may then vary between a few angstroms and a few hundreds of nanometers depending on the size of the nanostructures used initially. The intermediate tie layer 204 may itself be porous after elaboration via a microelectronics process. It should be noted that either the nanostructures 203 or the tie layer 204, or else both, may be porous.

Example 5

Preparation of Memory Cell with Charge Storage Molecules Comprising Functionalized Nanostructures (FIG. 4)

A substrate 401, known as a wafer base, produced according to procedures mainly as described in the prior art references is used. The latter is a silicon substrate 401, the sacrificial gate zones (402, 403, 404, 405, 406) and source zones 407 and drain zones 408 are defined. The total thickness of the layers 402, 403, 404 is, for example, around 100 to 500 nm and corresponds to the total thickness of the gates of a memory location. The pedestal layer 402 is an oxide produced by oxidation of the substrate. It is covered with the layer 403 of polycrystalline or amorphous silicon, itself protected by a silicon nitride layer 404. The gate zone is surrounded by a silicon oxide spacer 405 and a silicon nitride spacer 406. The source zones 407 and drain zones 408 are formed from a doped zone 409, produced by one or more implantations, for example of phosphorus or arsenic ion with a dose of $10^{13}$ to $10^{16}$ $cm^2$ at an energy of 3 to 5 keV, and from a silicided zone 410 in order to produce the electrical contacts. A thick layer 410 of a material was then deposited in order to encapsulate the device and was planarized by mechanochemical polishing down to the dummy (or sacrificial) gate, the silicon nitride layer 404 acting as a stop layer. The layer 410 in this example is an oxide layer. The layer 410 is either made from a conductive or insulating material and after polishing protects the source zones 407 and drain zones 408.

Figure 4A:
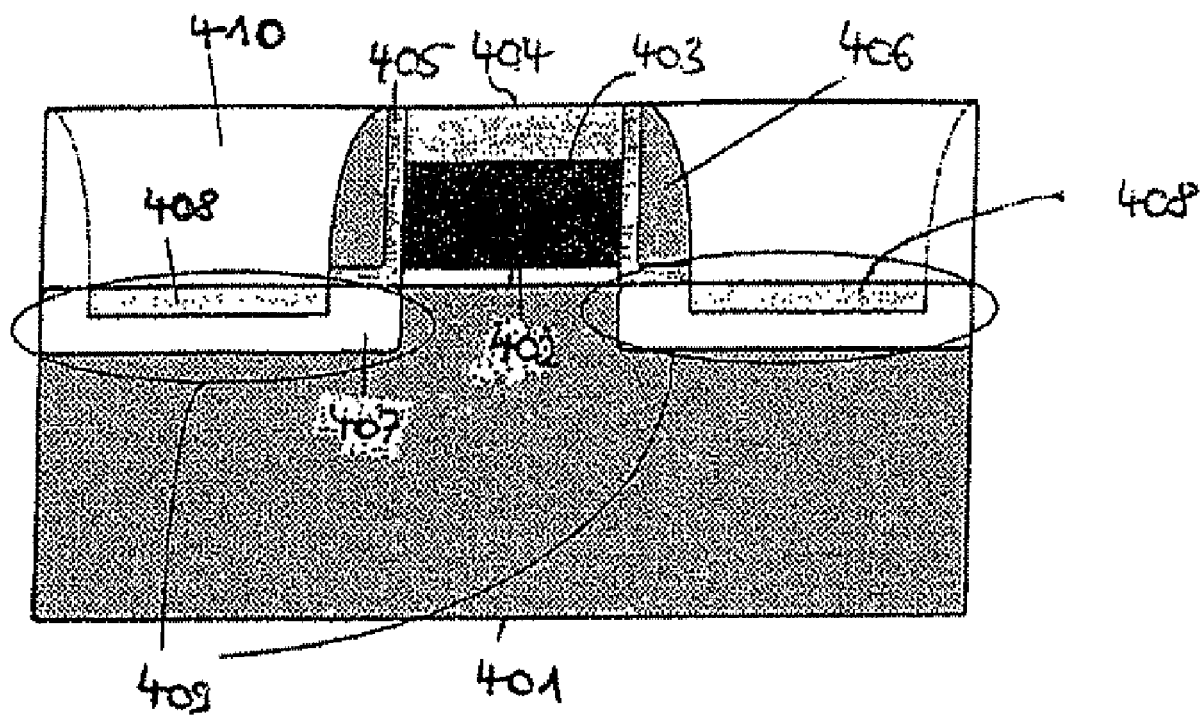
FIG. 4 illustrates the process according to the invention for manufacturing an electronic memory according to the invention.
Figure 4B:
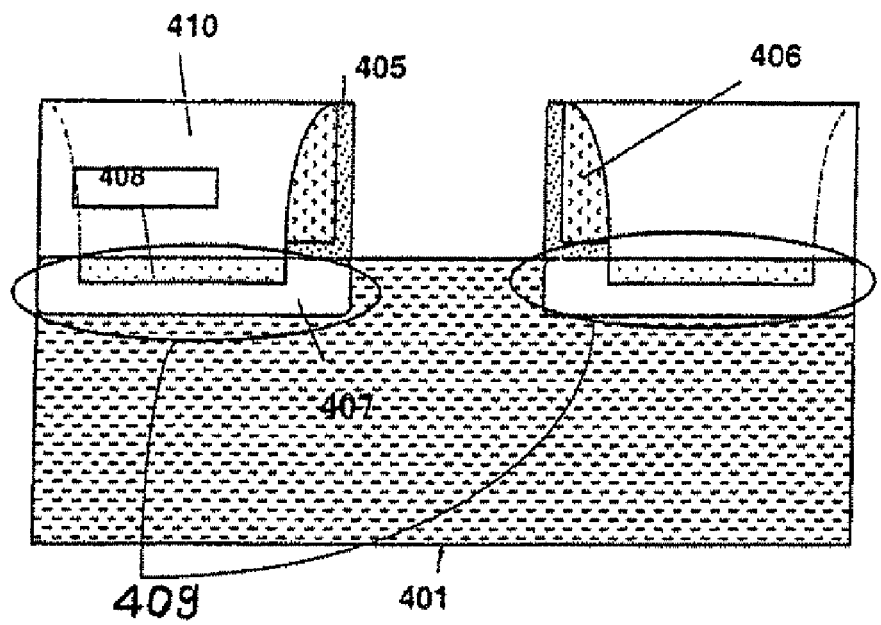

To carry out the invention, the first step consists in removing the dummy gate delimited by the side spacers 405 and 406 and surrounded by the encapsulation layer 410. The removal of the gate is carried out by successive etching of the layers 404 and 403, then of the pedestal layer 402 which, in the present example, is completely removed (FIG. 4B).

Figure 4C:
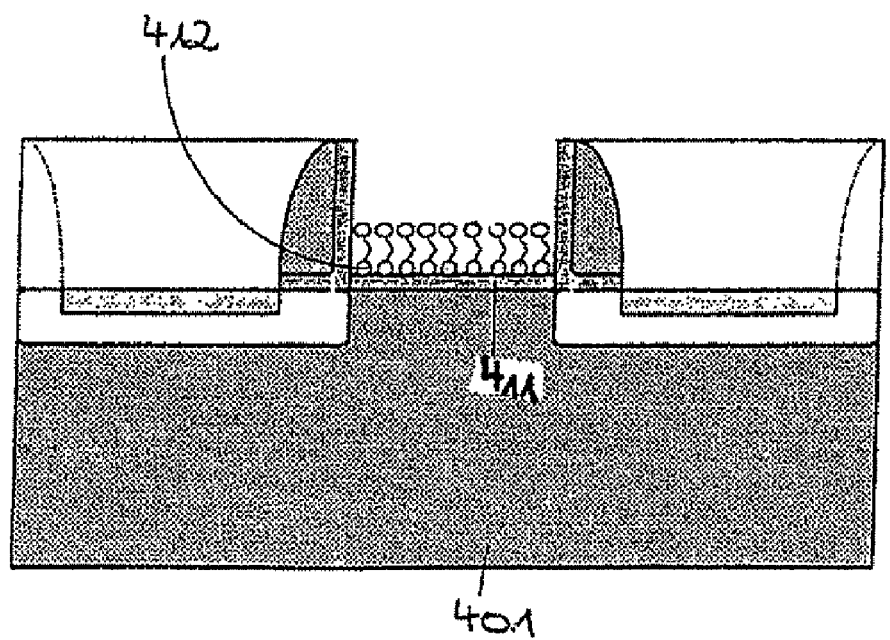

FIG. 4C illustrates the result of a first series of operations for producing the definitive gate. Firstly, an insulating layer 411 is formed at the bottom of the well 420 produced in the etching step. This is, for example, a silicon oxide that is deposited or obtained by oxidation of the underlying silicon substrate 401.

The nanostructured sites 412 are then deposited as described above. These are, for example, silicon nanodots produced by CVD using the 2-step process. After the deposition of the nanostructures 412, the organic molecules of interest 413 are grafted after pretreatment of the nanostructures 412 to produce a tie layer according, for example, to one of the procedures described above. The organic molecules 413 may be, for example, molecules having redox properties, that is to say that exist in at least two oxidation states such as metallocenes, metalloporphyrins, polyoxometallates, etc.

Figure 4D:
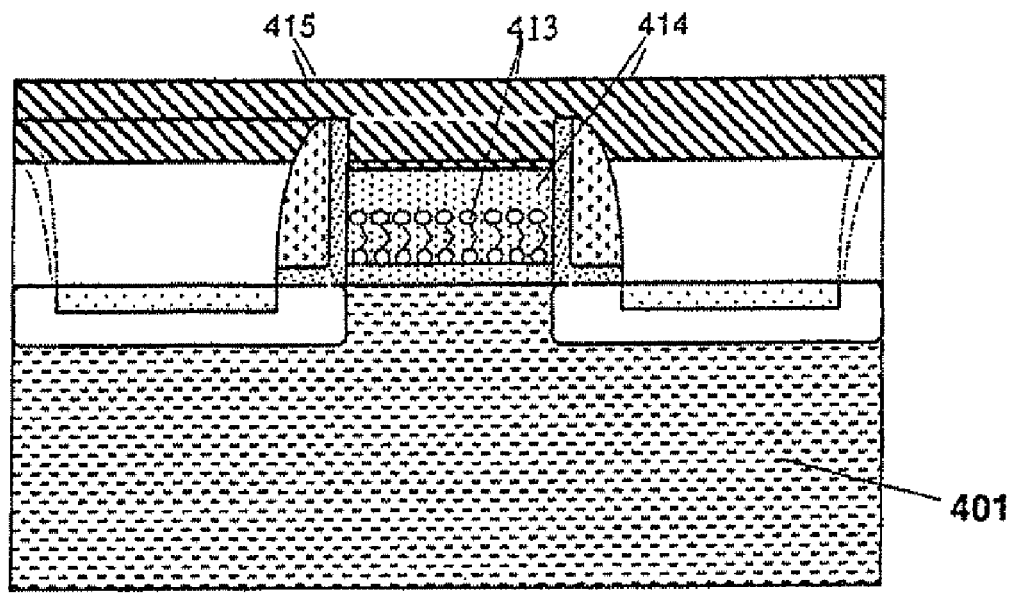

FIG. 4D describes a second series of operations to produce the control gate. The control dielectric 414, for example an oxide, produced at low temperature by microelectronics processing techniques, or an electrolyte gel, is deposited on top of the active organic molecules. Next, the control gate 415, made from a conductive material such as doped silicon or a metallic material used as a control gate material in the field of microelectronics, as described in the references is then deposited onto the control dielectric 414. The thickness of this layer is sufficient to completely fill the part of the well not yet occupied by the other layers of the definitive gate multilayer.

Figure 4E:
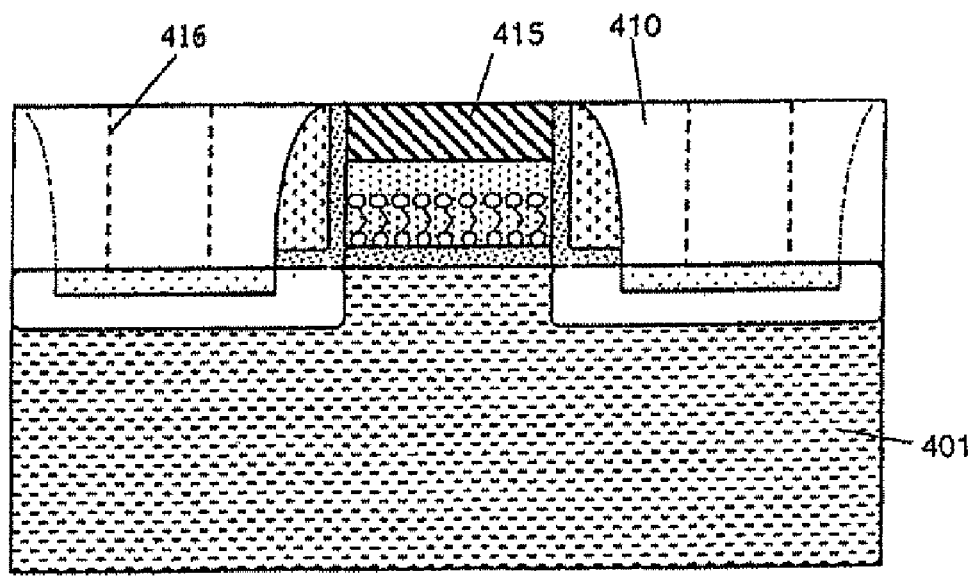

FIG. 4E shows the completion of the memory component. The deposition of the layer 415 is followed by a planarization which makes it possible to remove all the materials which jut out above the encapsulation layer 410 in order to bare its surface face. This operation completes the process for manufacturing the memory itself. It may however be completed by the interconnection of the memory component with other components produced on the same substrate or not. The production of these interconnections departs from the literal context of the exemplary embodiment of the invention. They are not described here. Only the dotted lines 416 indicate the position of the contacting passages which it is possible to produce in the layer 410 in order to connect the source and the drain to interconnection lines that are not represented.

The invention claimed is:

1. A nanostructured device (100), comprising a substrate (101), an intermediate layer (102), a zone (103) comprising a multitude of three-dimensional nanostructured sites (104), produced directly on the intermediate layer, in the form of grains, said nanostructures being capable of receiving chemical species (106) after the production of said sites,
   wherein the surfaces of the three-dimensional nanostructured sites (104) are equipped with a tie layer (204), which tie layer (204) is porous; or
   wherein the three-dimensional nanostructured sites (104) are separated from one another, and wherein the grains are porous.

2. The device as claimed in claim 1, wherein the chemical species are attached to the nanostructured sites (104) by covalent bonds.

3. A nanostructured device (100), comprising a substrate (101), an intermediate layer (102), a zone (103) comprising a multitude of three-dimensional nanostructured sites (104), produced directly on the intermediate layer, in the form of grains, said nanostructures being capable of receiving chemical species (106) after the production of said sites, wherein the three-dimensional nanostructured sites (104) are separated from one another, and wherein the grains are porous.

4. The device as claimed in claim 1, wherein the surface of the tie layer (204) is equipped with chemical coupling functional groups.

5. The device as claimed in claim 1, wherein the substrate (101) is a material comprising silicon, germanium, or quartz or a mixture thereof.

6. The device as claimed in claim 5, wherein the intermediate layer (102) is a dielectric or insulating material.

7. The device as claimed in claim 6, wherein the dielectric is selected from the group consisting of oxides, nitrides, oxynitrides, carbides, oxycarbides and silicates of Si, Al, Hf, Zr or Ti.

8. The device as claimed in claim 1, wherein the three-dimensional nanostructured sites (104) are grains having a hemispherical or spherical shape.

9. The device as claimed in claim 8, wherein the grains have a diameter between 2 and 150 nm.

10. The device as claimed in claim 9, wherein the density of the grains on the intermediate layer (102) is in the range between $10^6$ and $10^{12}$ $cm^{-2}$.

11. The device as claimed in claim 1, wherein the chemical species (106) are selected from the group consisting of nucleic acids, peptides, proteins, enzymes, antibodies, lipids, their biological partners, compounds having redox properties, metallocenes, metalloporphyrins and polyoxometallates.

12. A biochip comprising a multitude of devices as claimed in claim 1.

13. The device as claimed in claim 1, wherein the chemical species are covered with a dielectric layer.

14. The device as claimed in claim 13, wherein a layer made of a conductive material is located on top of the dielectric layer.

15. An electronic memory comprising a multitude of devices as claimed in claim 14 which are interconnected.

16. The electronic memory as claimed in claim 15, wherein the multitude of devices forms a control gate.

17. The electronic memory as claimed in claim 16 comprising a source and a drain.

18. The electronic memory as claimed in claim 17 having an encapsulation layer which is made of an electronically-conductive material or from an electrically-insulating material.

19. A process for manufacturing a device as claimed in claim 1, the process comprising the following successive steps:
   a) providing a substrate (101);
   b) forming an intermediate layer (102) on the surface of the substrate (101);
   c) producing three-dimensional nanostructured sites (104) directly on the intermediate layer (102) in the form of grains; and
   d) tying chemical species (106) to the surface of the three-dimensional nanostructured sites (104).

20. The process as claimed in claim 19, wherein a tie layer (204) is deposited on each nanostructured site (104).

21. The process as claimed in claim 20, wherein the tie layer is activated by treatment with a compound that has functional groups capable of attaching chemical species via a covalent bond.

22. The process as claimed in claim 19, wherein the chemical species (106) are selected from the group consisting of nucleic acids, peptides, proteins, enzymes, antibodies, lipids, their biological partners, compounds having redox properties, metallocenes, metalloporphyrins and polyoxometallates.

23. The process as claimed in claim 19, which achieves the manufacturing of an electronic memory (400), wherein the substrate (101) is made of silicon (401) and comprises sacrificial gate zones (402, 403, 404, 405, 406), sources (407), drains (408), a silicided zone (409) and an encapsulation layer (410).

24. The process as claimed in claim 23, the process comprising, before step b), the following step:

b₁) removing the sacrificial gate by the gate zone (405) down to the surface of the substrate (401) in order to form a well (420) of defined size.

25. The process as claimed in claim 24, wherein steps b) and c) are carried out by:
   b) forming an insulating layer (411) over the surface of the substrate (401) obtained in step b₁; and
   c) depositing nanostructured sites (412) over the insulating layer (411) at the bottom of the well (420).

26. The process as claimed in claim 25, further comprising the following additional steps:
   e) applying a layer (414) of a control dielectric over the tied chemical species; and
   f) depositing a layer (415) made from a conductive material over the control dielectric layer (414).

27. The process as claimed in claim 23, wherein the removal of the dummy gate is carried out by successive etching of layers 402, 403 and 404.

28. The process as claimed in claim 27, wherein the formation of the insulating layer is carried out by oxidation of the substrate (401).

29. The process as claimed in claim 28, wherein the deposition of nanostructured sites (412) is carried out by a CVD, LPCVD or inoculation/annealing method.

30. The process as claimed in claim 23, wherein a tie layer (414) is deposited on each nanostructured site (412).

31. The process as claimed in claim 30, wherein the tie layer (414) is activated by treatment with a compound that has functional groups capable of attaching chemical species via a covalent bond.

32. The process as claimed in claim 23, wherein the chemical species are molecules that have at least two stable oxidation states.

33. The process as claimed in claim 32, wherein the layer (414) of a control dielectric is formed by low-temperature deposition or by addition of an electrolyte gel.

34. A nanostructured device (100), comprising a substrate (101), an intermediate layer (102), a zone (103) comprising a multitude of three-dimensional nanostructured sites (104), produced directly on the intermediate layer, in the form of grains, said nanostructures being capable of receiving chemical species (106) after the production of said sites, wherein the surfaces of the three-dimensional nanostructured sites (104) are equipped with a tie layer (204), which tie layer (204) is porous.

35. A process for manufacturing a device as claimed in claim 34, the process comprising the following successive steps:
   a) providing a substrate (101);
   b) forming an intermediate layer (102) on the surface of the substrate (101);
   c) producing three-dimensional nanostructured sites (104) directly on the intermediate layer (102) in the form of grains,
   and depositing a tie layer (204) on each nanostructured site (104).

36. A biochip comprising a multitude of devices as claimed in claim 34.

37. The device as claimed in claim 3, wherein the surfaces of the three-dimensional nanostructured sites (104) are equipped with a tie layer (204), wherein the tie layer (204) is porous.

38. A process for manufacturing a device as claimed in claim 3, the process comprising the following successive steps:
   a) providing a substrate (101);
   b) forming an intermediate layer (102) on the surface of the substrate (101); and
   c) producing three-dimensional nanostructured sites (104) directly on the intermediate layer (102) in the form of grains.

39. A biochip comprising a multitude of devices as claimed in claim 3.

* * * * *